United States Patent [19]

Gaenzler et al.

[11] 4,147,718
[45] Apr. 3, 1979

[54] METHOD FOR MAKING METHACRYLIC ACID, ITS NITRILE AND ITS ESTERS

[75] Inventors: Wolfgang Gaenzler, Darmstadt-Arheilgen; Klaus Kabs, Seeheim; Guenter Schroeder, Ober-Ramstadt, all of Fed. Rep. of Germany

[73] Assignee: Rohm GmbH, Darmstadt, Fed. Rep. of Germany

[21] Appl. No.: 869,605

[22] Filed: Jan. 16, 1978

[30] Foreign Application Priority Data

Jan. 20, 1977 [DE] Fed. Rep. of Germany ....... 2702187

[51] Int. Cl.² .................. C07C 121/32; C07C 57/04; C07C 69/54
[52] U.S. Cl. .............................. 260/465.9; 260/561 N; 560/211; 562/599
[58] Field of Search ..................... 260/465.9, 526 N; 560/211; 562/599

[56] References Cited

U.S. PATENT DOCUMENTS

| | | | |
|---|---|---|---|
| 3,051,747 | 8/1962 | Leathers et al. | 260/526 N |
| 3,089,898 | 5/1963 | Vitcha et al. | 560/210 |
| 3,247,248 | 4/1966 | Sims et al. | 260/526 N |
| 3,440,276 | 4/1969 | Wolf et al. | 560/210 |
| 3,578,702 | 5/1971 | Snapp, Jr. et al. | 260/465.9 X |
| 3,654,345 | 4/1972 | Jentsch | 560/210 |
| 3,840,587 | 10/1974 | Pearson | 560/210 |
| 3,933,888 | 1/1976 | Schlaefer | 560/210 X |

FOREIGN PATENT DOCUMENTS 2457993 6/1976 Fed. Rep. of Germany.
2615887 10/1977 Fed. Rep. of Germany.

*Primary Examiner*—Joseph Paul Brust
*Attorney, Agent, or Firm*—Curtis, Morris & Safford

[57] ABSTRACT

In the method of making a compound of the formula

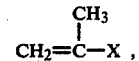

wherein X is carboxyl, a carboxylic acid ester group —COOR₂, or cyano, by reaction of a compound of the formula CH₃CH₂X with methylal in the presence of a catalyst, the improvement wherein said catalyst is a catalyst system which consists essentially of (1) silicon dioxide dosed with a basic component and (2) a member selected from the group consisting of aluminum oxide and titanium dioxide.

6 Claims, No Drawings

METHOD FOR MAKING METHACRYLIC ACID, ITS NITRILE AND ITS ESTERS

The present invention relates to a method for making methacrylic acid, its nitrile, and esters of this acid from propionic acid, propionitrile, or from esters of propionic acid.

Methacrylic acid and its functional derivatives are of considerable technical importance, for example, as monomeric starting products for polymerization. A means already proposed to arrive at $\alpha,\beta$-unsaturated carboxylic acids and their functional derivatives involves the reaction of the corresponding alkanoic acids or their derivatives with formaldehyde. A series of catalysts has been proposed for this type of reaction. Certain problems result from the activation of formaldehyde. For example, although alkali catalysts or alkali-dosed catalysts increase the activity of formaldehyde, at the same time the tendency toward undesired side reactions also increases.

Recently a method for making methacrylic acid as well as esters and the nitrile of this acid was proposed in German Offenlegungsschrift No. 2,457,993, in which propionic acid, its esters, or propionitrile is reacted with methylal. The reaction is carried out under catalysis by aluminum oxide or a catalyst containing aluminum oxide.

The condition of the aluminum oxide influences the reaction. It is recommended in the aforementioned German patent publication to use thermally pre-treated aluminum oxide. The results reported indicate a certain opposition between catalytic activity and selectivity when aluminum oxide which has been heated at temperatures in the region from 600° C. to 1100° C. is employed.

When highly-tempered aluminum oxide is employed, conversion decreases while selectivity increases. The aforementioned patent publication comes to the conclusion that the reaction of propionic acid with methylal, as a prototype of the process, proceeds according to a different mechanism than does the reaction of propionic acid with formaldehyde. Various mechanisms for the reactions of formaldehyde and of methylal are immediately plausible according to this theory if one proceeds, for example, from the fact that methylal under basic conditions is normally extremely slow to react, entirely in contrast to formaldehyde. As evidence of the differently-proceeding mechanism in the formation of methacrylic acid from propionic acid and methylal, the German patent publication points to the experimentally-determined finding that pyrogenic silicic acid dosed with alkali hydroxide shows almost no catalytic effect for the formation of methacrylic acid from propionic acid and methylal.

It has been found that the reaction of methylal with propionic acid or with its esters or nitrile to form methacrylic acid or the corresponding esters or nitrile of this acid can surprisingly be increased if, within the same reaction batch, silicon dioxide with basic components is used as well as an aluminum oxide catalyst and/or a catalyst containing titanium dioxide.

The silicon dioxide catalysts which can be employed according to the invention are suitably prepared from finely divided silicon dioxide having high surface area. Catalysts prepared from silicon dioxide aerogels are particularly suitable (cf. "Ullmann's Encyclopaedie der techn. Chemie", by W. Foerst, 3d ed. Vol. 15, p. 725–727, Urban & Schwarzenberg, Munich-Berlin, 1964). The use of pyrogenically-obtained silicon dioxide aerogels is preferred. These materials are commercially available under the tradenames "Aerosil" and "Cab-O-Sil" [cf. Angew. Chem 72–744 (1960)]. Pyrogenically-obtained silicon dioxide is also known as "pyrogenic silicic acid".

The basic compounds which are to be used as the basic component of the silicon dioxide catalyst within the scope of the present invention include, in addition to organic bases, principally inorganic bases, particularly compounds of a metal of Group IA or IIA of the Periodic System of the elements which react basically or are transformed by calcination into basic compounds. These compounds may optionally be used in admixture. In this connection can be named the alkali metals and alkaline earth metals such as sodium, potassium, rubidium, magnesium, calcium, strontium, barium, and cesium, particularly sodium hydroxide, potassium hydroxide, cesium hydroxide, calcium carbonate, calcium hydroxide, sodium oxalate, sodium amide, and cesium silicate. The alkali hydroxides, particularly potassium hydroxide and cesium hydroxide, are particularly preferred.

Within the scope of the present invention, those aluminum oxides which have been pretreated for catalytic use come first into consideration as aluminum oxide catalysts. Supplemental dosing of the aluminum oxide catalyst is possible. However, dosing of the aluminum oxide catalyst can be dispensed with in the normal performance of the invention.

The aluminum oxide catalysts to be employed according to the invention, particularly in the case of commercially available materials of natural origin, may contain metal oxides such as $Fe_2O_3$, $TiO_2$, and $Na_2O$.

Further possibilities for the coating or dosing of the catalysts, i.e. of the aluminum oxide and/or of the titanium dioxide, involve the use of salts, including acid salts, such as the alkali metal and alkaline earth metal phosphates, the alkali metal and alkaline earth metal borates, and water-soluble zinc salts such as zinc chloride or zinc sulfate.

Pretreatment of the aluminum oxide catalysts includes a thermal pretreatment at temperatures from about 250° C. and 1100° C., especially tempering at a temperature from 600° C. to about 1000° C. This pretreatment is described in German Offenlegungsschrift No. 2,457,993 and can be adopted for purposes of the present invention.

The titanium dioxide catalysts which can be used in addition to or in place of the aluminum oxide catalyst can contain the various modifications of titanium oxide such as rutile or anatase and may optionally contain further components (dosing). The use of rutile is preferred.

For dosing or coating the titanium oxide, as already mentioned, predominantly a material containing a salt, including acid salts, comes into question, for example the alkali metal phosphates, alkali metal borates, and water soluble zinc salts.

The titanium dioxide catalyst may be used without thermal pretreatment or may be thermally pretreated at a temperature between 250° C. and 1100° C.

The silicic acid to be employed according to the present invention must have a basic component, i.e. the silicic acid is treated in a known fashion with basic compounds. For example, a solution of the base, for example an aqueous solution, can be made into a slurry or paste with the silicic acid. Suitably a paste is prepared with stirring and, optionally, with heating, which paste is then dried or calcined. The drying temperature is suitably above the evaporation temperature of the solvent, about 130° C. when water is used. The period of drying is dependent upon the amount of material to be dried. Subsequently, tempering between about 320° C. and 460° C. is recommended.

It can be desired to preform the silicic acid in a definite way. Dosing of the silicic acid with from 0.25 to about 5% by weight of base, preferably with about 1 to 2% by weight of base has proved particularly useful technically.

The total amount of catalytically active material is dependent in the first instance on the size of the reactor.

The ratio of the amount of silicon dioxide containing a basic component to the aluminum oxide catalyst or to the titanium dioxide-containing catalyst can vary between certain limits, for example within the weight ratios 70:30 to 10:90. Under practical conditions, a weight ratio of approximately 1:1 is suitable.

The process of the present invention can be carried out technically as in German Offenlegungsschrift No. 2,457,993. For example, the reactors described in the aforementioned publication can be used.

The reactors must permit the catalysts according to the present invention to exert their effect in one and the same reaction batch, either separated from one another or in admixture: the catalyst can be viewed as a system comprising silicon dioxide having basic components, preferably pyrogenic alkali-dosed silicon dioxide, together with an aluminum oxide catalyst and/or a titanium dioxide-containing catalyst.

The loading of the reactor can follow with layering as well as with internal mixing of the two kinds of catalysts. The layer thickness will be conformed to a certain degree to the dimensions of the installation or to the amounts involved in the reaction, but is not really critical according to the present experience. Within reactors having the dimensions of those shown in the following examples (throughput of about 250 ml/hour, calculated on the liquid reaction solution, with a heatable length of the quartz reactor of 72 cm and an internal diameter of 4 cm), a layer thickness of about 10 cm satisfies the requirements in a very satisfactory way. The reaction is as a rule carried out in a reactor at a temperature between 250° C. and 500° C.

It is directly apparent to one skilled in the art that in the reaction under consideration methylal reacts with an activated carbon atom in the α-position of a compound of the formula $R_1CH_2X$ with addition of a carbon atom (by C—C bonding and formation of a double bond). In the formula, X is a carboxyl group, an ester group -$COOR_2$, an acid amide group -$CONR_3R_4$, or a cyano group, and $R_1$ is alkyl or alkaryl. It is further clear that as concerns the meaning of $R_2$, no limitation on the operability of the reaction is to be expected, except in the case where $R_2$ would itself be reactive under the reaction conditions. From a practical viewpoint, those compounds are preferred wherein $R_2$ is optionally-branched alkyl having 1 to 20 carbon atoms. Compounds wherein $R_2$ is alkyl having 1 to 8 carbon atoms, particularly methyl, ethyl, propyl or butyl, are especially preferred.

The product

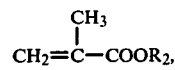

wherein $R_2$ stands for methyl (i.e. methylmethacrylate), is a key technical substance from which other compounds, wherein $R_2$ stands for a higher alkyl group, can be prepared by known methods, for example by transesterification.

Similarly, there are no limitations on $R_3$ and $R_4$ except that the groups be stable under the reaction conditions. Preferably $R_3$ and $R_4$ are hydrogen or have the same meaning as $R_2$.

Similarly, $R_1$ can represent groups which are essentially inert under the reaction conditions and which offer no steric hindrance which would make the reaction difficult. From a practical viewpoint, alkyl groups are preferred. Particularly preferred is the compound wherein $R_1$ is methyl, that is, propionic acid and its functional derivatives, including propionitrile.

The ratio of the reagents can vary within certain limits in the process according to the invention. In general, the mol ratio of the compound $R_1CH_2X$ to methylal is from 1:1 to 10:1, preferably 1:1 to 5:1.

The reaction of a propionic acid ester with methylal can also proceed in such a fashion that, instead of the ester, propionic acid together with at least an equivalent amount of alcohol is employed. This is particularly applicable in the case of propionic acid methyl ester.

The reaction according to the invention in this case can be described by the following equation:

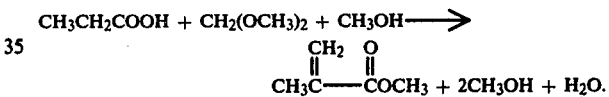

In every case, an ester product is present in equilibrium with the corresponding free acid. In case the preparation of a compound of the formula $R_1CH_2X$, wherein X is a carboxyl group, i.e. an acid or a salt derived therefrom, is the sole object in practicing the method of the invention, a hydrolysis step and, optionally, a neutralization/salt-formation employing a base providing the desired cation can be appended to the catalytic process step. The hydrolysis (and, optionally, the salt-formation) can be carried out in a manner known per se, for example by subjecting the condensed reaction product to an acid-catalyzed hydrolysis.

The process according to the present invention represents a significant advance in comparison with the state of the art. From a technical viewpoint, the present invention pertains to the preparation of technically-desirable products of the formula

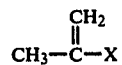

wherein X has its aforementioned meaning, by reaction of a compound of the formula

with methylal using silicon dioxide having a basic component with an aluminum oxide catalyst and/or a titanium oxide-containing catalyst within the same reaction batch.

It is possible according to the method of the invention to increase the yield of propionic acid compounds, in comparison with reactions known in the art and using aluminum oxide as the catalyst, to such an extent that the possibilities for realization can be technically decisive.

A better understanding of the invention and of its many advantages will be had by referring to the following specific examples, given by way of illustration.

The following data pertain to all the examples:
(a) Preparation of the catalyst
(1) Thermal pretreatment of the aluminum oxide Solid cylinders of aluminum oxide were tempered for 10 hours at 900° C. for thermal pretreatment.

(2) Dosing of the silicic acid

Pyrogenic silicic acid was formed into a dough with very dilute 1% aqueous potassium hydroxide solution, dried for 5 hours at 130° C., and subsequently tempered for another 10 hours at 450° C. in a drying oven. In following Example 12, the ratio of 1 percent aqueous potassium hydroxide to pyrogenic silicic acid is about 1:1 Results comparable to those in Example 12 are obtained using 0.3 percent and 1.8 percent aqueous potassium hydroxide or cesium hydroxide solution.

(b) Performing the process
(1) Catalytic reaction of methyl propionate with methylal A reaction mixture comprising methyl propionate and methylal was introduced into an evaporator (temperature about 200° C.) from a storage vessel with the aid of a dosage pump. A quartz tube 30 cm. long and 3 cm. in diameter filled with saddle bodies can be used as the evaporator. On leaving the evaporator, the gaseous reaction components are introduced with a constantly-maintained nitrogen stream into a quartz reactor filled with the catalyst. The quartz reactor has a heatable length of 72 cm and an internal diameter of 4 cm. The filling volume, calculated on the catalyst, is about 800 ml. The measuring point of the thermal element is located at about half the height of the catalyst. The gases leaving the reactor are immediately cooled with an intensive condenser. Analysis of the gas mixture can be carried out gas chromatographically (2 meter steel column filled with 4% XE 60 on Chromosorb G as the column packing).

Quantitative evaluation follows according to the method of internal standards. The values given in the following examples are given in weight percent.

Instead of methyl propionate and methylal, propionic acid, methanol, and methylal can be used in the reaction.

(c) Charging of the reactor 400 ml. of aluminum oxide are filled into the reactor together with 400 ml. of the alkali-dosed pyrogenic silicic acid prepared according to the process (a). Filling can take place in layers as well as by an internal admixture of both kinds of catalyst. The thickness of a catalyst layer in the following examples is about 10 cm. The throughput of liquid reaction solution can be about 250 ml/hour.

The results obtained by maintaining the conditions under (a)-(c) above are given in Table I for Examples 1-11.

TABLE I

Throughput: 250 ml/h of reaction solution and 30 l/h of nitrogen.
Preheating temperature: 200° C.
Reactor temperature: 420°–460° C.

| Ex. No. | Reactor Temp. (° C.) | Reaction Mixture | Conversion of Propionic Acid or Methyl propionate (%) | Selectivity - Formation of Methylmethacrylate (%) |
|---|---|---|---|---|
| 1 | 410 | A | 11.5 | 33.3 |
| 2 | 420 | A | 13.6 | 34.4 |
| 3 | 430 | A | 9.6 | 70.7 |
| 4 | 440 | A | 11.5 | 95.4 |
| 5 | 450 | A | 14.2 | 81.0 |
| 6 | 460 | A | 24.1 | 55.2 |
| 7 | 420 | D | 7.2 | 83.3 |
| 8 | 440 | D | 14.2 | 79.8 |
| 9 | 460 | D | 32.1 | 50.9 |
| 10 | 440 | B | 13.3 | 87.1 |
| 11 | 440 | C | 42.0* | 78.1 |

*Conversion based on 1/5th of the methyl propionate used.
Reaction Mixture:
A = Propionic acid: methanol: methylal = 1:1:1
B = Methyl propionate: methylal = 1:1
C = Methyl propionate: methylal = 5:1
D = Propionic acid: methanol: methylal = 1:1.5:1

EXAMPLE 12

The pyrogenic silicic acid dosed with KOH is mixed with the Al$_2$O$_3$. Reaction mixture B is added under the conditions of Examples 1–11 at 420° C. The conversion obtained therewith amounts to 32.7%. The methacrylate selectivity = 48.8%.

EXAMPLE 13

Instead of aluminum oxide, titanium dioxide (rutile) is used which is mixed with pyrogenic silicic acid in a volume ratio of 1:1. After tempering the catalyst at 500° C., reaction mixture B is introduced over the contact in a reactor at 400° C. under conditions analogous to those in Examples 1–12. Methyl methacrylate is obtained.

EXAMPLE 14

Preparation of methacrylonitrile

The catalyst, experimental procedure, and reaction conditions are the same as in Example 1.

With a mixture of propionitrile and methylal in a mol ratio of 1:1, a propionitrile conversion of 18 percent is obtained with a methacrylonitrile selectivity of 85 percent.

EXAMPLE 15

Preparation of methacrylic acid by hydrolysis

The reactor contents of Example 4 (500 g) are combined with 180 ml of water and with 20 g of an acid ion exchanger commercially available under the tradename "Amberlite IR-120". After the addition of 2 g of hydroquinone as a stabilizer, the mixture is heated in an apparatus comprising a distillation column (7 theoretical plates) with a reflux ratio of 3:1. The methanol formed and the methylal are distilled off through the head.

The mixture remaining in the sump comprising methacrylic acid and unreacted propionic acid is distillatively separated in a known fashion. The reaction is quantitative.

EXAMPLE 16

Equal portions by volume of titanium dioxide (rutile), of pyrogenic silicic acid (dosed with 1% aqueous potassium hydroxide solution) and of aluminum oxide (tempered at 600° C.) are mixed intimately and filled into the reactor as described above. Under the same conditions as given in Table 1, reaction mixture B is applied onto the catalyst at 400° C. The conversion of propionic methyl ester amounts to 18%. The methylmethacrylate selectivity =58%.

What is claimed is:

1. The method of making a compound of the formula

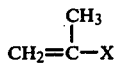

which comprises reacting methylal with a compound of the formula $CH_3CH_2X$, where X is carboxyl, cyano, or a carboxylic acid ester group inert under the reaction conditions, at a temperature between 250° C. and 500° C. in the presence of a catalyst system which consists essentially of (1) 10 to 70 percent by weight of silicon dioxide dosed with a basic compound of a metal of Group IA or Group IIA of the Periodic System and (2) to 30 percent by weight of a member selected from the group consisting of titanium dioxide and thermally pretreated aluminum oxide.

2. A method as in claim 1 wherein said member (1) is pyrogenic silicon dioxide.

3. A method as in claim 2 wherein said basic compound is potassium hydroxide or cesium hydroxide.

4. A method as in claim 1 wherein said aluminum oxide is thermally pretreated at a temperature above about 250° C.

5. A method as in claim 1 wherein said aluminum oxide is thermally pretreated at a temperature above 600° C.

6. A method as in claim 1 wherein the reaction is carried out at a temperature from 420° C. to 460° C.

* * * * *